United States Patent [19]
Weckström

[11] Patent Number: 6,001,064
[45] Date of Patent: Dec. 14, 1999

[54] CORRECTION OF A MIXTURE GAS EFFECT IN MEASURING BASED ON RADIATION ABSORPTION

[75] Inventor: Kurt Peter Weckström, Espoo, Finland

[73] Assignee: Instrumentarium Oy, Helsinki, Finland

[21] Appl. No.: 08/929,957

[22] Filed: Sep. 15, 1997

[30] Foreign Application Priority Data

Sep. 18, 1996 [FI] Finland .................... 963693

[51] Int. Cl.[6] .................................................. A61B 5/00
[52] U.S. Cl. ............................ 600/532; 73/23.3; 422/84
[58] Field of Search .................... 600/529, 532; 73/19.01, 19.02, 19.04, 19.05, 23.21, 23.24, 23.27, 23.37, 23.3; 422/83, 84

[56] References Cited

U.S. PATENT DOCUMENTS

| | | | |
|---|---|---|---|
| 4,379,402 | 4/1983 | Harman, III ........................ | 73/23 |
| 4,423,739 | 1/1984 | Passaro et al. . | |
| 5,282,473 | 2/1994 | Braig et al. ........................ | 600/532 |
| 5,311,447 | 5/1994 | Bonne . | |
| 5,445,160 | 8/1995 | Culver et al. ...................... | 600/532 |
| 5,457,320 | 10/1995 | Eckles et al. . | |

FOREIGN PATENT DOCUMENTS 2218804  11/1989  United Kingdom .

OTHER PUBLICATIONS

Journal of Applied Physiology, vol. 25, No. 3, 1968, pp. 333–335, G. Ammann, Problems Associated with the Determination of Carbon Dioxide by Infrared Absorption.

E. O. Doebelin: *Measurement Systems*, McGraw–Hill, Kogakusha, 1976, pp. 465–475.

Sensors and Actuators A49 (1995) pp. 103–108, H. Andrews, Damping and Gas Viscosity Measurements Using a Microstructure.

*Primary Examiner*—Robert L. Nasser
*Attorney, Agent, or Firm*—Andrus, Sceales, Starke & Sawall

[57] ABSTRACT

A measuring device for determining the concentration of such gas components from a gas mixture, which includes collision dilation of the absorption lines constituting the absorption spectral bands for measuring objects. The device comprises a non-dispersive concentration measuring sensor (20), which includes: a measuring chamber (6) containing a gas mixture to be analyzed; a radiation source (17) for emitting over a wavelength range which includes an absorption spectral band used in concentration determination; a detector (18) receiving radiation that has passed through the measuring chamber and for producing a first signal (7) therefrom; as well as an optical bandpass filter (16) positioned between the detector and the radiation source. The measuring device further comprises a second measuring sensor (4) for identifying the viscosity or some other viscosity-related feature of a gas mixture to be analyzed and for producing a second signal (9). Both signals (7, 9) are delivered to a calculating unit (8), which uses at least a second signal for performing the corrections required for the first signal. In addition, the device is provided with a display means (10).

23 Claims, 2 Drawing Sheets

CORRECTION OF A MIXTURE GAS EFFECT IN MEASURING BASED ON RADIATION ABSORPTION

BACKGROUND OF THE INVENTION

The present invention relates to a method for determining in a gas mixture the concentration of at least one gas component, which gas mixture contains or may contain component materials which cause collision dilation or boardening of the absorption lines constituting the absorption spectral band of the gas component, said method comprising: (a) providing a radiation source for emitting radiation through a gas mixture to be analyzed over a wavelength range, in which is included the absorption spectral band used in the concentration measuring of said gas component, providing the path of radiation progressing through the gas mixture with an optical bandpass filter, having a transmission band which positions itself in line with said spectral band and using a detector for detecting the radiation that has passed through the gas mixture and the optical bandpass filter; (b) carrying a first signal produced in the detector by this intensity to a calculating unit for obtaining a first result based on non-dispersive radiation absorption measuring. The invention relates also to a measuring device for implementing this method.

When measuring a gas concentration with infrared technique, the most common practice is to use a non-dispersive method, which means that the absorption signal is measured over a narrow wavelength range, i.e. through an optical bandpass filter provided with a narrow transmission band. Thus, the measured signal representing the radiation that has passed through a sample and an optical filter will be an integrated value of transmissions occurring at various wavelengths of the band. The absorption spectrum of a gas in molecular state normally consists of absorption bands produced by molecular vibrations and of a fine structure, i.e. absorption lines, resulting from rotational transitions inside the molecule. Thus, when measured at a sufficient resolution, the absorption spectrum of a gas consists of a large number of very narrow absorption lines. For example, carbon dioxide has a vibration absorption range, whose spectral band has a mean wavelength of 4260 nm. A more accurate analysis confirms that the band consists of more than 80 narrow absorption lines produced by rotation. These lines have a half-value width and intensity which are dependent on several factors, such as temperature, self-absorption resulting from a long measuring path, and collisions by other molecules included in a gas mixture. The first two are generally quite easy to account for in the compensation of a measuring signal by measuring the temperature and the linearization effects on a gas in question caused by measuring geometry. On the other hand, the alteration resulting from collisions by other gas components, i.e. a mixture gas effect, which sometimes can be significant, must be taken very carefully into consideration for the minimization of concentration errors.

The publication JOURNAL OF APPLIED PHYSIOLOGY, Vol. 25 No. 3, 1968, pp. 333–335: Ammann, Galvin—"Problems associated with the determination of carbon dioxide by infrared absorption" discloses how the measured concentration value of carbon dioxide changes in different gas mixtures. The obtained result is typical when measuring is effected nondispersively with an optical filter having a narrow transmission band, said transmission band extending, as per normal, across several rotational lines. In the collisions of gas molecules, the energy spectrum of a rotational transition increases, resulting in the dilation or broadening of an absorption line. In measuring, it is detected as an increased absorption, even if the absorbances of rotational lines integrated across the measuring band were in fact invariable. This is due to the fact that the object of measuring is transmission instead of absorbance. The absorbance value, which is calculated on the basis of transmission and which is proportional to concentration, differs from a correct value just enough to overestimate the concentration. If the calibration of carbon dioxide is performed by using a nitrogen compound therefor, as in the cited publication, the concentration measured for certain other gas mixtures is too high and for others it is too low.

Especially polar gases, such as nitrous oxide, have a major effect on the line width. The magnitude of a concentration error is also influenced by the length of a measuring duct. With a short duct, i.e. with a short absorption length for a gas mixture to be measured, the demand for compensation is lesser whereas with a longer duct, wherein the absorption of a gas to be measured has decreased transmission substantially more, the demand for compensation can be considerable. When measuring e.g. carbon dioxide from the alveolar air of a patient, whereby a considerable portion of the gas mixture may consist of nitrous oxide (laughing gas), the calculated concentration value can be even 15% too high as a result of the above-explained error caused by transmission measuring. Therefore, for example, compensation of the amount of carbon dioxide measured in the alveolar air of a patient is conducted by measuring separately the content of laughing gas and by implementing on the basis thereof a mathematical correction of the carbon dioxide concentration, as described in the publication U.S. Pat. No. 4,423,739. Likewise, the effect of oxygen and the effect of anesthetic gases used during anesthesia are often compensated for although, in practice, the error caused thereby is slightly lesser. A problem with the method described in the cited publication is that all gases contributing to the collision dilation must be measured separately or concentrations of the gases must be otherwise known. This is inconvenient and unreliable, especially since the mixture includes varying amounts of hard-to-measure gases, such as nitrogen or in some cases helium or argon.

The publication GB 2,218,804 endeavours to provide a correction signal for the collision dilation by measuring thermal conductivity. It seems that the collision dilation produced by nitrous oxide in carbon dioxide is presented in the cited publication in a wrong direction. In reality, when the concentration of nitrous oxide rises, the measured absorption of carbon dioxide increases and this, in turn, increases the uncompensated concentration of carbon dioxide. In fact, there is no evidence to indicate that thermal conductivity in general would actually correlate in any way with collision dilation, although this seems to be the case in terms of the discussed gas mixture. Nitrous oxide has a low thermal conductivity, which must be proportioned to its major contribution in carbon dioxide in terms of promoting collision dilation. However, nitrogen and oxygen have both roughly the same thermal conductivity, although nitrogen contributes more than oxygen towards collision dilation. A result of this is that in alveolar air, for example, a measuring error of $CO_2$ resulting, for example, from various concentrations of oxygen cannot be corrected. As an example, a measuring process has been applied to a mixture containing 5% of carbon dioxide in nitrogen, oxygen, and nitrous oxide by using a non-dispersive infrared measuring device. Relative to the tendency of nitrogen to dilate the absorption lines of carbon dioxide, it was confirmed that oxygen yielded 6% lower concentration values for carbon dioxide. On the other hand, nitrous oxide yielded carbon dioxide with values that were 7% too high. This can be contributed to the fact that oxygen has a thermal conductivity which is just 0.7% higher than that of nitrogen, while nitrous oxide has a thermal conductivity which is 37% lower than that of nitrogen. This leads to a conclusion that it is totally impossible to create a reliable correction method by the application of thermal conductivity. In addition, there are anomalies, such as hydrogen, which has a very high thermal conductivity, but still has a collision-dilation promoting effect on carbon dioxide which is even stronger than that of nitrous oxide.

BRIEF SUMMARY OF THE INVENTION

Thus, an object of this invention is to provide a method for correcting an error caused by the above-described collision dilation in a normal non-dispersive concentration measuring system for gas mixtures, wherein the transmission band of an optical bandpass filter has a width that exceeds the width of an absorption line included in the spectral band of a gas to be examined. The object is to provide a method affording a correction that is sufficiently accurate and properly oriented for practical measuring situations, when the actual concentration of a gas component is measured as described. A second object of the invention is a method of the above type, which is highly suitable for the analysis of alveolar air and especially for the analysis of respiratory air for surgical patients.

The above drawbacks can be eliminated and the above objects are achieved by means of a method of the invention, which is characterized by what is set forth in the claims, and by means of a measuring device of the invention, which is characterized by what is set forth in the claims.

It has been surprisingly discovered that the exploitation, according to a method of the invention, of a correction factor derived from the measured viscosity of a gas mixture can be used for producing a signal which can be used for compensating for errors caused by collision dilation, regardless of the type of mixture gas. This correction factor is used for correcting the non-dispersively measured concentration of a gas component. Thus, there is no necessity to measure the concentrations of all participating gases, even though different gases have a different contribution to collision dilation.

BRIEF DESCRIPTION OF THE SEVERAL VIEWS OF THE DRAWING

The invention will now be described in detail with reference made to the accompanying figures.

FIG. 1 illustrates a collision frequency $\Gamma$ for various gases as a function of viscosity a.

DETAILED DESCRIPTION OF THE INVENTION

In molecular collisions, a gas mixture experiences a momentum transfer and a weak interaction, as a result of which the energy levels and, respectively, energy transitions or spectral lines dilate or spread. The weak interaction can be a dipole—dipole interaction, if both molecules have some dipole moment but most of the interaction is of the type dipole-polarization or polarization-polarization interaction, whereby also non-polar molecules or even atoms may be involved in the process. In the vicinity of another molecule, a non-polar gas molecule polarizes or the outermost electron shell of a gas atom deforms slightly, thus resulting in a weak interaction. Hence, in practice, all molecules may contribute to the collision dilation of a spectral line and also atomic gases, such as noble gases, have a contribution, although a minor one.

Figure 1:
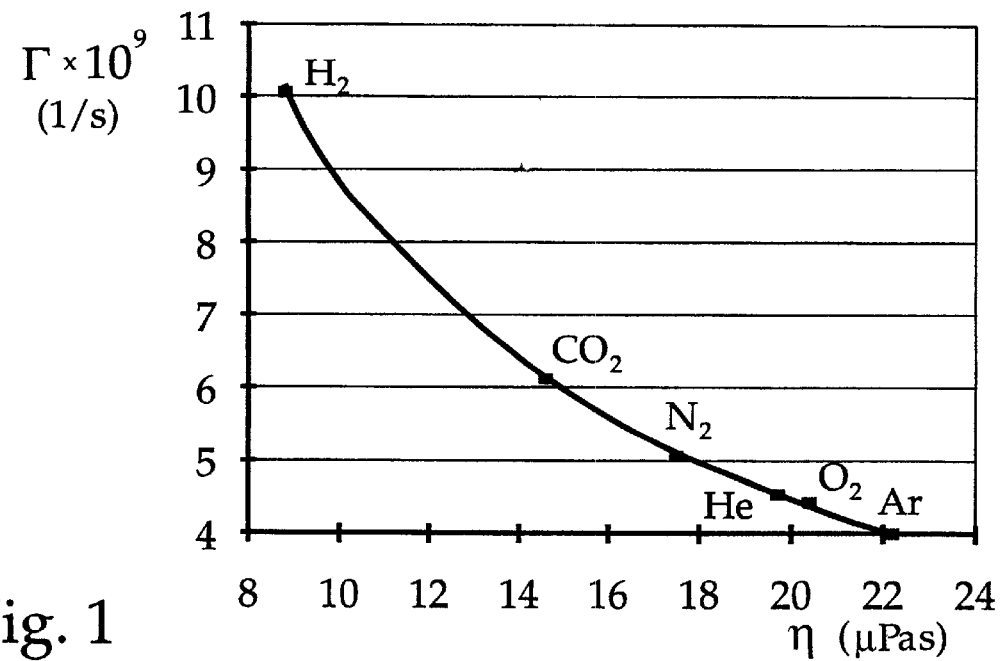

The more often collisions occur, the more spectral lines obviously dilate. Thus, the collision dilation is in correlation with the collision frequency $\Gamma$, which is $$\Gamma = v_{ave}/l$$

wherein $v_{ave}$ represents the average speed of a molecule and l is the clear distance for a molecule between collisions. The gas viscosity $\eta$ is determined according to the formula $$\eta = (1/3) \cdot n \cdot m \cdot v_{ave} \cdot l$$

wherein n is the number of molecules in unit volume and m is the mass of a molecule, When this is supplemented with the clear distance l worked out from the collision-frequency expression and it is taken into consideration that, for an ideal gas, the average molecular speed will be $$v_{ave} = (8kT/\pi m)^{1/2},$$

the viscosity will be expressed by $$v = (8kT/3\pi\Gamma),$$

wherein k represents the Boltzmann constant and T is temperature. Thus, the viscosity is dependent on the collision frequency and temperature and, hence, on the collision dilation as well. FIG. 1 illustrates clearly this correlation for such gases as: hydrogen ($H_2$), carbon dioxide ($CO_2$), nitrogen ($N_2$), helium (He), oxygen ($O_2$), and argon (Ar). The values shown in FIG. 1 are known as such in the literature, but the conclusions, upon which the invention is based, have not been drawn from those values.

Figure 2:
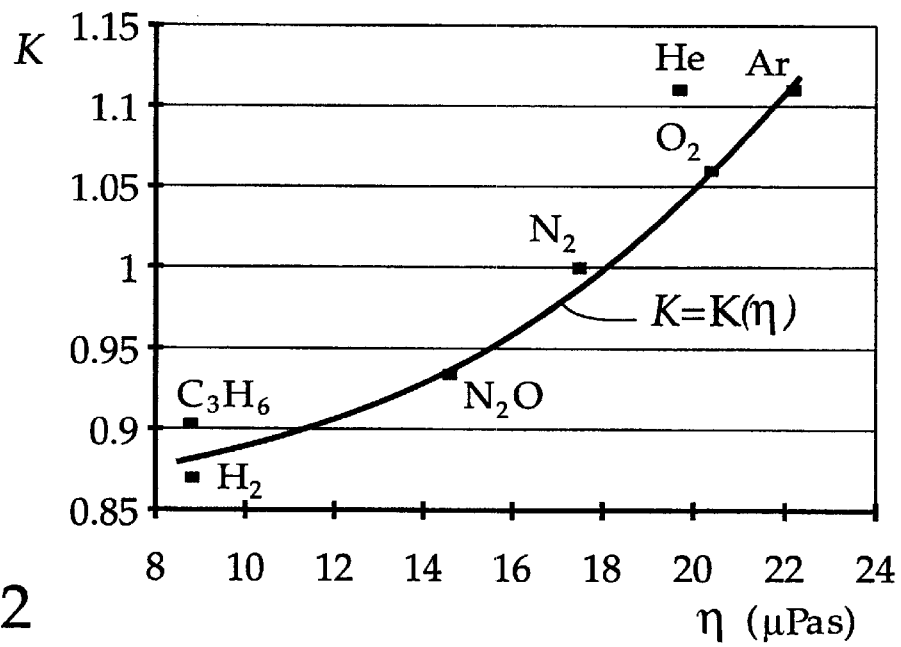
FIG. 2 illustrates a relationship between the viscosity $\eta$ of various gas mixtures containing $CO_2$ and a balance gas and a factor K required for correcting the collision dilation of carbon dioxide.

If the value of gas viscosity and the collision dilation are dependent upon each other, this should be obvious e.g. from a delineator therebetween. FIG. 2 illustrates a measured factor K required for correcting the concentration of carbon dioxide as a function of the viscosity $\eta$ of such mixture gases as hydrogen ($H_2$), laughing gas ($N_2O$), cyclopropane ($C_3H_6$), nitrogen ($N_2$), oxygen ($O_2$), argon (Ar), and helium (He). In FIG. 2, the factor K has been determined for a gas mixture, having a carbon dioxide concentration of 5% and the rest consisting of the above-mentioned gas and, thus, it can be expressed as a function of viscosity $K=K(\eta)$. A correct concentration c is obtained by multiplying a measured concentration $c_m$ by the factor K, hence $$c = K(\eta) \cdot c_m$$

The factor K must be compensated for the variations of temperature T and, if necessary, it can possibly be compensated also for some property of a gas mixture, such as for a composition $c_x$, if the concentration correction is not sufficiently accurate otherwise. If measurements are made at various absorption bands, the factor K can also be determined for various wavelength ranges, i.e. for various applied absorption bands. Thus, the factor has a value which is a function of these different variables, such as $K(\eta,\lambda)$ in regard to viscosity and wavelength, $K(\eta,T)$ in regard to viscosity and temperature, $K(\eta,c_x,T)$ in regard to viscosity, composition, i.e. concentrations $c_x$ of one or a few contributing gas components determined by some appropriate means, as well as temperature etc., according to which possible contributing factors are taken into consideration at a given time. Furthermore, if desired, these factors K can be given what at any given time is a closest suitable predetermined value $K_i(\eta)$ or a value $[K_i(\eta)+(K_{i+1}(\eta))]/m_x$, which is interpolated from predetermined values and in which $m_x$ represents a value depending on that quantity of those quantities, relative to which the interpolation is carried out, according to a mathematical procedure generally known as interpolation. It is obvious that this selection or interpolation can be applied to any of the above-described combination factors $K(\eta,\lambda)$, $K(\eta,T)$, $K(\eta,c_x,T)$ etc. In FIG. 2, the viscosity values are values of pure balance gases, but on the basis of conducted examinations, it seems that the replacement of values relating to pure gases with values theoretically more consistent with the practical situation does not change the function K significantly at least in all situations. Even if, in practice, it were necessary to adopt the effect of a mixture gas, such as carbon dioxide, on the total viscosity, it is still always possible to find an experimental correlation for determining the factor $K(\eta)$ or a corresponding combination factor therefrom. Thus, the factor function $K=K(\eta, ...)$ of the invention is determined experimentally beforehand for each application of a device and its requirements and programmed into a calculating unit 8 included in the device. This prior conducted determination can be carried out, for example, by using a test gas mixture or mixtures prior known in terms of the composition thereof. These test gas mixtures contain typically the same component materials as those probably included in a gas mixture to be analyzed. It is also possible to provide the test gas mixtures with component materials which develop in the absorption lines of a gas component to be determined a dilation of the lines of the absorption spectral bands of the gas component which is similar to what in reality happens in a gas mixture to be analyzed.

It has been confirmed that the correction factor of a given gas mixture is not exactly equal to the average of the correction factors of pure gas components as weighted by the concentrations thereof. Likewise, the viscosity of a gas mixture is not equal to the weighted average of the viscosity values of gas components unlike, for example, the density of a gas mixture. The correction requirement of a collision dilation may vary over various infrared-absorption ranges depending on how the energies are distributed in a collision. In addition, some gases may behave abnormally, depending on which gas mixture they are included and on which gas molecule they have an impact as a result of collisions. Especially the light and polar hydrogen gas is included in this category. While having a major impact on the infrared absorption of carbon dioxide, as shown in FIG. 2, its effect on a certain infrared-absorption range of methane is in the same order as that of oxygen, i.e. relatively insignificant. In cases like this, it may be difficult to find a straightforward correlation between the viscosity of a gas mixture and the required correction factor. In most cases, however, the employed gas mixtures behave regularly and a straightforward determination of the correction factor is possible. This is the case e.g. in a respiratory gas mixture, which during the course of anesthesia, may contain oxygen, nitrogen, carbon dioxide, laughing gas, and various anesthetic gases. The anesthetic gases are heavy halogenated hydrocarbons which, in terms of a collision dilation, behave the same way as cyclopropane in FIG. 2. Occasionally, pulmonary examinations also involve the use of helium. The use of a correction factor according to the curve $K(\eta)$ shown in FIG. 2 would mean that the corrected carbon dioxide concentration would be loo low, yet more accurate than the uncorrected concentration. On the hand, helium also behaves slightly irregularly in mixtures. The total viscosity may be higher than the viscosity of any gas component and, therefore, the use of total viscosity would yield a correction factor that would be closer to the correct value than what is implicated by FIG. 2.

The measuring of viscosity can be effected in a variety of ways. It is possible that some other viscosity-related measurable quantity can be used for determining a correction factor. Since the viscosity of a gas is a sort of internal friction, it is natural to measure the same from a flowing gas and directly from the flow thereof. Unless the gas mixture possess a sufficient flow, the sensor itself may create vibratory or rotational motion or other movement, which produces a flow whose changes will be measured. It is also possible to measure the characteristics of such vibratory or rotational movement or other motion directly, such as the resistance caused by a gas mixture relative thereto or to the components creating these motions. Another possibility is to measure changes in a pressure or sound wave created in a gas. For example, the quality factor of a cavity in the state of resonance, i.e. the absorption of resonance, depends on the internal friction or viscosity of a gas, whereas the resonance frequency depends on the dimensions of a cavity. This measuring technique may involve the use of a continuous sound signal or a sputter type of signal, which in most cases is sinusoidal. A non-sinusoidal pressure signal can also be used by measuring, over a given distance, the rising and/or falling edge of a pressure wave for distortions, which are also dependent on the internal friction of a gas, i.e. the viscosity. The distortion can be calculated e.g. from the fact that the outgoing pressure wave has a Fourier expansion which is different from that of a received wave for thereby calculating the viscosity. Of course, there are also other ways of determining the viscosity value from such a modified pressure signal.

The measuring of viscosity in a flowing gas mixture can be effected, for example, by measuring a pressure difference across a laminar-flow pipe according to the formula $$\eta = C_L \cdot \Delta p_L / Q$$

known from the literature, wherein $C_L$ represents a constant depending on the dimensions of a pipe, $\Delta pL$ is a pressure difference measured across the pipe, and Q is a volume flow. If the volume flow Q is kept constant or otherwise known, it is easy to obtain a value directly proportional to viscosity by measuring a pressure difference created across the pipe.

Figure 3:
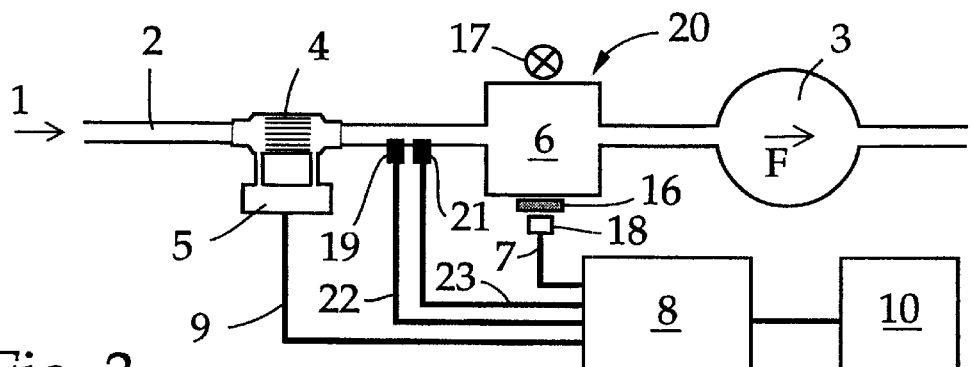
FIG. 3 shows a first embodiment for a measuring system used in the analysis of gas mixtures, employing a viscosity value to be measured from a gas mixture for the correction of a collision dilation.

At its simplest, the measuring system is as shown in FIG. 3. A sample gas 1 travels as a flow F in a sample tube 2 aspirated e.g. by a pump 3. The device includes a prior known or novel type of non-dispersive optical measuring sensor 20, provided with a chamber 6 for running the gas flow F therethrough. Thus, the non-dispersive measuring sensor 20 includes the measuring chamber 6 which contains the gas mixture 1 to be analyzed, as well as a radiation source 17 for emitting radiation through the measuring chamber over a wavelength range, which includes the applied absorption spectral band of a gas component to be determined in terms of its concentration. In addition, the sensor includes in this case a single detector 18, which is positioned to receive radiation transmitted through the measuring chamber, as well as an optical bandpass filter 16, fitted between the detector and the radiation source and having a transmission band which extends within the absorption spectral band of a gas component to be measured over the area of several absorption lines, as explained earlier in this text. This concentration measuring sensor 20 uses non-dispersive infrared absorption to measure at least a gas component subject to correction. Coupled with the flow F is, in this case in series with the non-dispersive concentration measuring sensor 20, a laminar flow element 4 and a differential pressure sensor 5. The laminar flow element and the differential pressure sensor can be for example of a type described in the publication E. O. Doebelin: MEASUREMENT SYSTEMS, McGraw-Hill Kogakusha, 1976, but it can also be of another prior known or novel type. A measuring signal 7 received from the detector 18 of the concentration measuring sensor 20 is delivered to the calculating unit 8, wherein it is normally linearized and compensated from temperature and pressure changes. For such compensation, the path of the flow F is provided at some suitable point, in this case between the laminar flow element 4 and the optical concentration measuring sensor 20, with a temperature sensor 19 and an absolute-pressure measuring pressure sensor 21 included in the flow duct. A signal 9 obtained from the pressure difference sensor 5 as well as a signal 22 obtained from the temperature sensor 19 and a signal 23 received from the absolute-pressure detecting sensor 21 are also forwarded to the calculating unit 8 for calculating the correction factor K and for correcting the signal 7 coming from the concentration measuring sensor 20 both in terms of temperature and pressure and the error caused by a collision dilation as described above, prior to showing the result on a display unit 10. The laminar flow element 4 and the concentration measuring sensor 20 need not necessarily be connected in series, as shown in the figures, but they can be separate circuits as long as both receive a similar sample gas.

Figure 4:
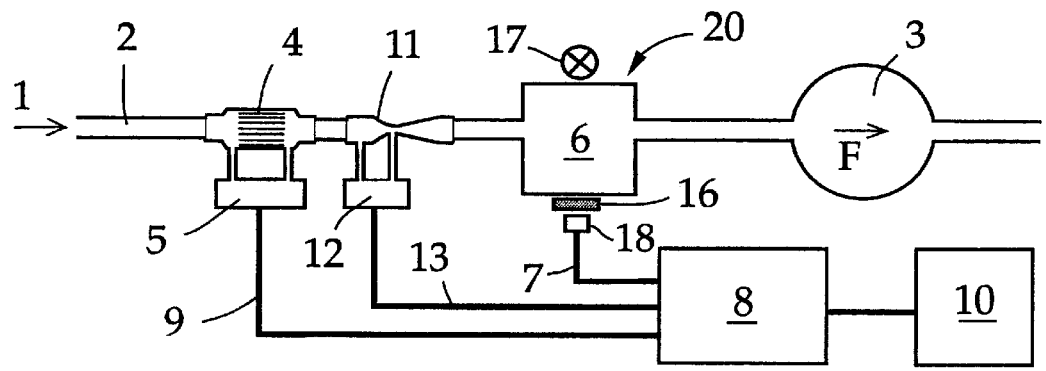
FIG. 4 shows a second embodiment for a measuring system used in the analysis of gas mixtures, employing a viscosity value to be measured from a gas mixture as well as some other measurable quantity for the correction of a collision dilation
Figure 5:
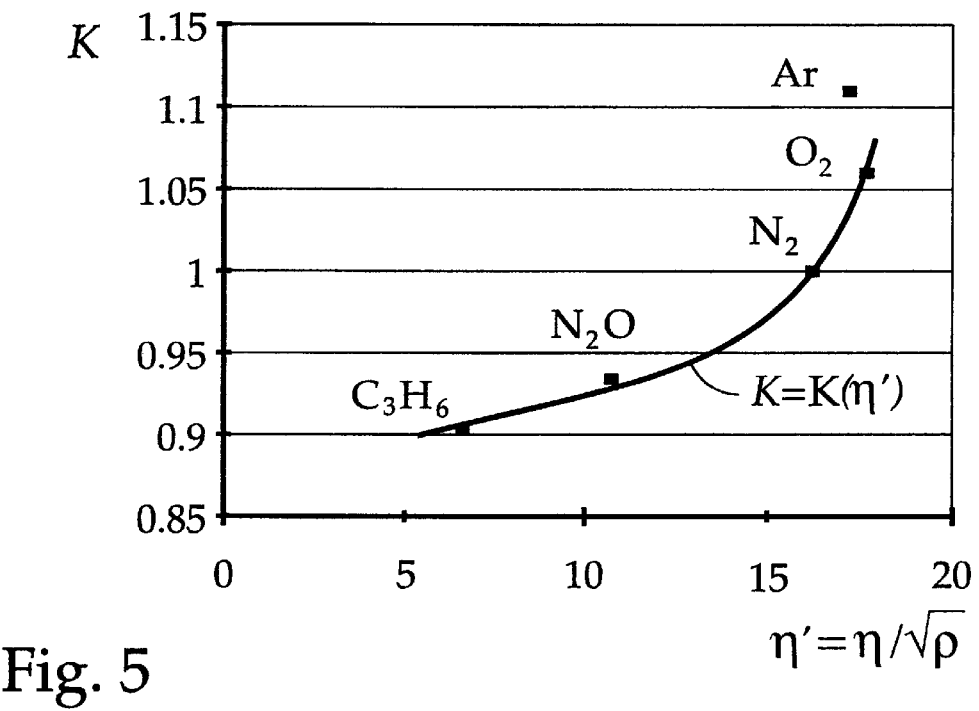
FIG. 5 illustrates a relationship between a measurable apparent viscosity value $\eta'$ depending on the viscosity of a balance gas of various gas mixtures and a factor K required for correcting the collision dilation of carbon dioxide.

A problem in the case shown in FIG. 3 may be the volume flow Q, which is not necessarily known. It can be measured in a variety of ways, as described in the publication E. O. Doebelin: MEASUREMENT SYSTEMS, McGraw-Hill Kogakusha, 1976. For example, the Bernoulli-type flow meters, based on a pressure change caused by a barrier included in a flow, can be used for measuring the volume flow Q according to the formula $$Q = C_T \cdot (\Delta PT/\rho)^{1/2}$$

wherein $C_T$ represents a constant depending on dimensions, $\Delta PT$ is a difference of the pressure measured at the inlet duct and the barrier, and $\rho$ is the density of a gas mixture. If the density is known or can be calculated on the basis of the composition of a gas mixture, the volume flow Q can be calculated and included in the above viscosity formula, by means of which the viscosity $\eta$ is calculated on the basis of measuring values obtained from the laminar flow sensor 4, 5. This type of measuring system is depicted in FIG. 4, wherein a flow sensor 11 is coupled in series with the laminar flow sensor 4, 5, the flow F being equal through both. A differential pressure sensor 12 delivers a signal 13 to the calculating unit 8 for obtaining viscosity according to the formula $$\eta = C \cdot \Delta p_L \cdot (\rho/\Delta p_T)^{1/2}$$

wherein a constant C is a combination of the previously discussed constants. If the density $\rho$ is not known, the result will be the following expression of the apparent viscosity $\eta'$ $$\eta' = C \cdot \Delta p_L / \Delta PT^{1/2},$$

which in some cases may be good enough for the determination of a correction factor. FIG. 5 illustrates the correction factor K required by the concentration measurement reading of carbon dioxide as a function of said expression $\eta'$, whereby the measured values can be accommodated with a function $K = K(\eta')$. In the case of light gases, such as hydrogen and helium, the correction does not work, whereby helium could be determined to have a maximum value in terms of the function $K(\eta')$ and thereby an approximately proper correction factor. Another alternative is to employ a flow meter independent of density or to measure the density separately and to perform thereafter a calculation for determining the real viscosity $\eta$. In arrangements, wherein the volume flow is a quantity having a direct or indirect impact on the viscosity value TI or the apparent viscosity value $\eta'$, the volume flow is also measured from that flow of sample gas 1 which is used for measuring the viscosity, apparent viscosity or some other feature of a gas mixture serving as a determination basis thereof.

Figure 6:
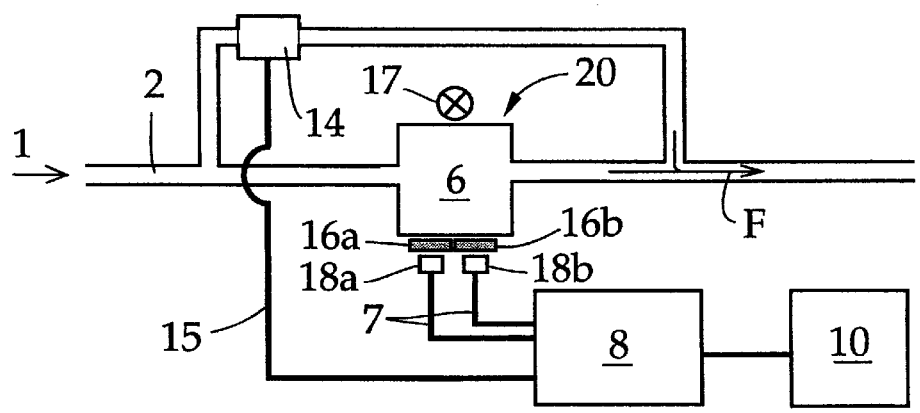
FIG. 6 shows a second embodiment for a measuring system used in the analysis of gas mixtures, employing a viscosity value to be measured from a gas mixture for the correction of a collision dilation and wherein the non-dispersive absorption measuring is conducted by using a plurality of filter-detector pairs.

If it desirable to measure viscosity by means of vibration or resonance technique, it is possible to employ for example such a micromechanical version of viscosity sensor, which is described in the publication SENSORS AND ACTUATORS A 49 (1995) pp. 103–108: Andrews, Harris—"Damping and gas viscosity measurements using a microstructure". The principle of coupling such a viscosity sensor with a measuring system of the invention is depicted in FIG. 6, wherein a signal 15 produced by a viscosity sensor 14 is carried to the calculating unit 8 for determining the above-described correction factor K. A phase reversal $\Phi$ occurring in a control frequency $\omega$ of the sensor 14 is directly proportional to viscosity according to the formula $$\tan\Phi = C_M \cdot \eta \cdot \omega$$

wherein $C_M$ represents a constant depending on dimensions and the elastic constant. According to the publication, the resulting value of viscosity must be compensated for in terms of pressure, if necessary. In this case, the viscosity sensor 14 is positioned relative to the flow F in parallel with the concentration measuring sensor 20, but of course it could also be positioned in series with the concentration measuring sensor 20. By virtue of its compact size, the viscosity sensor 14 could also be integrated with the concentration measuring sensor 20, for example in the measuring chamber 6. In the embodiment of FIG. 6, the concentration measuring sensor includes two optical bandpass filters 16a and 16b as well as two detectors 18a and 18b, respectively, for eliminating other disturbance factors appearing for example in optical measurements. The additional filter-detector pair 16a, 18a or 16b, 18b can of course be also used for the analysis of some other gas component, i.e. for identification and/or determination of concentration. It is obvious that, whenever necessary, the concentration measuring sensor 20 may include even a higher number of filter-detector pairs or a higher number of filters coupled with a single detector or with a lower number of detectors for eliminating errors occurring in optical measuring and for analyzing a plurality of gas components. Also other such viscosity sensors, which produce a result that is not dependent on the volume flow of a gas mixture, can be positioned alongside the concentration measuring sensor 20 relative to the gas mixture flow F. This type of high-speed viscosity sensors are particularly preferred in such cases that the flow F changes quickly and/or irregularly, whereby the viscosity sensor can be positioned relative to the concentration measuring sensor 20 either in series or in parallel.

As pointed out earlier, the gas viscosity can also be determined by using changes occurring in pressure, such as a sound wave or ultrasound. It is obvious that also other types of sensors for measuring the viscosity of a gas mixture or quantities correlated therewith are possible to construct and to use for correcting an error appearing in a gas concentration measured by the application of an infrared-absorption method and caused by collision dilation.

In case some other component of the apparatus takes care of the gas flow F, it is not necessary to use a separate pump, as shown in FIG. 6. On the other hand, the pump 3 in the embodiments of FIGS. 3 and 4 can be used to replace other pump equipment. Regardless of whether the viscosity sensor is coupled relative to the non-dispersive concentration measuring sensor 20 in parallel or in series, it is preferably positioned in any case as close as possible to the concentration measuring sensor, such that the gas mixture 1 to be analyzed would be as accurately as possible at the same temperature and/or pressure and/or in the same state in terms of some other quantity. Most of the time, the above description has used the term factor about a correction quantity K for collision dilation but, depending on various variables, the question may also be about some other form of correction quantity, such as a sum quantity, a polynomic form of quantity, or some other function. In general terms, the correction quantity K is thus some function of viscosity TI and other possibly contributing factors.

I claim:

1. A method for determining the concentration of a given gas by means of the absorption of radiation, the given gas being present in a gas mixture which may contain other gases causing collision broadening of absorption lines in the absorption spectrum of the given gas, said method comprising the steps of:

providing a sample of the gas mixture;

passing radiation through the gas mixture, the radiation having a wavelength range including an absorption spectral band for determining the concentration of the given gas;

filtering the radiation in the radiation path to form a radiation transmission band from said absorption spectral band;

detecting the filtered radiation to provide an output in accordance with the detected radiation;

making an initial determination of the concentration of the given gas from the detected radiation output based on radiation absorption;

measuring the viscosity of the gas mixture or a quantity related to gas mixture viscosity;

generating a gas concentration correction factor which is a function of the measured viscosity or viscosity related quantity; and applying the correction factor to the initial concentration determination to alter the initial determination to a final determination of the concentration of the given gas in the gas mixture which is compensated for the effects of collision broadening in the absorption spectrum of the given gas.

2. A method as set forth in claim 1 wherein the generating step is further defined as generating a correction factor which comprises the combination of the viscosity or viscosity related quantity measurement and a correlating factor (K).

3. A method as set forth in claim 2 further including the step of determining the correlating factor (K) by measuring a gas mixture of known composition.

4. A method as set forth in claim 2 further including the step of determining the correlating factor (K) to account for one or more of the following conditions under which the method is carried out: the absorption spectral band of radiation used in the method; the concentration range of the given gas in the gas mixture; the concentration range of another gas in the gas mixture; and the temperature of the gas mixture.

5. A method as set forth in the claim 2 further defined as predetermining values of the correlating factor (K) for given sets of conditions under which the method may be carried out and as determining the correlating factor (K) for the conditions under which the method is actually carried out by use of a predetermined value of the correlating factor (K) for conditions nearest to those under which the method is actually carried out.

6. A method as set forth in claim 2 further defined as predetermining values of the correlating factor (K) for given sets of conditions under which the method may be carried out and as determining the correlating factor (K) for the conditions under which the method is actually carried out by interpolation from the predetermined values of the correlating factor (K).

7. A method as set forth in claim 1 wherein the step of providing a gas mixture sample is carried out at a location and wherein the step of measuring the viscosity of the gas mixture is carried out proximate to said location.

8. A method as set forth in claim 1 wherein the step of measuring viscosity is further defined as measuring one of the flow characteristics of the gas mixture, the resistance to vibratory or rotational movement exhibited by the gas mixture, or the pressure wave transmission properties of the gas mixture.

9. A method as set forth in claim 8 wherein the method is further defined as determining the concentration of a given gas comprising $CO_2$ in a gas mixture comprising the respiratory gases of a subject.

10. A method as set forth in claim 1 wherein the method is further defined as determining the concentration of a given gas in a gas mixture comprising the respiratory gases of a subject.

11. A method as set forth in claim 1 wherein the method is further defined as determining the concentration of a given gas comprising $CO_2$.

12. A measuring device for determining the concentration of a given gas in a mixture of gases, said device employing absorption of radiation and providing an output compensated for the effects of collision broadening of absorption lines in the absorption spectrum of the given gas, said measuring device comprising:

a measuring chamber (6) for containing the gas mixture to be analyzed;

a radiation source (17) providing radiation in a radiation path, the radiation having a wavelength range including an absorption spectral band for determining the concentration of the given gas, said measuring chamber being located in said radiation path so that radiation from said radiation source passes through said measuring chamber;

an optical bandpass filter (16) for filtering the radiation in said radiation path, said filter having a transmission bandwidth including at least a selected portion of said absorption spectral band;

a detector (18) located in said radiation path for receiving filtered radiation passing through said sample chamber and providing an output in accordance with the received radiation;

determining means (8) coupled to said detector for making an initial determination of the concentration of the given gas in the gas mixture from the output of said detector based on radiation absorption;

means (4, 5, 1) for measuring the viscosity of the gas mixture or a quantity related to gas mixture viscosity; and means (8) coupled to said measuring means for generating a correction factor which is a function of the viscosity or viscosity related quantity, said determining means altering the initial determination responsive to the correction factor to produce an output indicative of a final determination of the concentration of the given gas in the gas mixture which is compensated for the effects of collision broadening in the absorption spectrum of the given gas.

13. A measuring device as set forth in claim 12 wherein said measuring means comprises one of a laminar flow sensor, oscillation absorption sensor, or a gas resonance sensor.

14. A measuring device as set forth in claim 12 wherein said measuring device further includes sensing means comprising at least one of a gas mixture pressure sensor, gas mixture temperature sensor, and gas mixture flow volume sensor, said sensor being coupled to said correction factor generating means for use in generating the correction factor.

15. A measuring device as set forth in claim 14 wherein said measuring chamber and said sensing means are proximate to each other.

16. A measuring device as set forth in claim 14 wherein said measuring chamber, said measuring means and said sensing means are proximate to each other.

17. A measuring device as set forth in claim 12 wherein said measuring chamber and said measuring means are proximate to each other.

18. A measuring device as set forth in claim 12 wherein said measuring device includes means providing a flow path for the gas mixture and wherein said measuring chamber and measuring means are connected in series in said flow path.

19. A measuring device as set forth in claim 12 wherein said measuring device includes means providing a flow path for the gas mixture and wherein said measuring chamber and measuring means are connected in parallel in said flow path.

20. A measuring device as set forth in claim 12 further including a pump for moving gas through the measuring chamber.

21. A measuring device as set forth in claim 12 further including a plurality of filters and detectors for determining the properties of a plurality of gases.

22. A measuring device as set forth in claim 12 further defined as a device for determining the concentration of a given gas comprising $CO_2$.

23. A measuring device as set forth in claim 22 further defined as a device for determining the concentration of a given gas comprising $CO_2$ in a gas mixture comprising the respiratory gases of a subject.

* * * * *

UNITED STATES PATENT AND TRADEMARK OFFICE
CERTIFICATE OF CORRECTION

PATENT NO. : 6,001,064
DATED : December 14, 1999
INVENTOR(S) : Kurt Weckström

It is certified that error appears in the above-identified patent and that said Letters Patent is hereby corrected as shown below:

Column 9,
Line 50, after "radiation" insert -- along a radiation path and --;

Column 10,
Line 22, delete "the"

Column 11,
Line 19, delete "(4, 5, 1)" and substitute therefor -- (4, 5, 14) --;

Signed and Sealed this

Twelfth Day of November, 2002

Attest:

Attesting Officer

JAMES E. ROGAN
Director of the United States Patent and Trademark Office